United States Patent
Leysieffer et al.

(10) Patent No.: US 6,736,770 B2
(45) Date of Patent: May 18, 2004

(54) IMPLANTABLE MEDICAL DEVICE COMPRISING AN HERMETICALLY SEALED HOUSING

(75) Inventors: Hans Leysieffer, Taufkirchen (DE); Dirk A. Fiedler, Ismaning (DE)

(73) Assignee: Cochlear Limited, Lane Cover (AU)

(*) Notice: Subject to any disclaimer, the term of this patent is extended or adjusted under 35 U.S.C. 154(b) by 35 days.

(21) Appl. No.: 09/938,493

(22) Filed: Aug. 27, 2001

(65) Prior Publication Data

US 2002/0051551 A1 May 2, 2002

(30) Foreign Application Priority Data

Aug. 25, 2000 (DE) ........................................ 100 41 728

(51) Int. Cl.$^7$ .............................................. H04R 25/00
(52) U.S. Cl. .............................. 600/25; 607/36; 607/56; 607/57; 607/429; 607/7
(58) Field of Search ................................. 128/899, 903; 600/25; 607/9, 36, 37, 39, 55, 56, 57, 34; 206/703, 705, 438, 570; 29/825, 830, 832, 842, 846, 854, 592.1, 594; 429/7, 8, 63, 176, 183

(56) References Cited

U.S. PATENT DOCUMENTS

| | | | |
|---|---|---|---|
| 3,557,775 A | | 1/1971 | Mahoney |
| 3,712,962 A | | 1/1973 | Epley |
| 3,764,748 A | | 10/1973 | Branch et al. |
| 3,926,198 A | | 12/1975 | Kolenik |
| 3,942,535 A | | 3/1976 | Schulman |
| 4,269,905 A | * | 5/1981 | Wedlake ............ 429/121 |
| 4,352,960 A | | 10/1982 | Dormer et al. |
| 4,441,210 A | | 4/1984 | Hochmair et al. |
| 4,616,655 A | * | 10/1986 | Weinberg et al. ............ 257/734 |
| 4,846,191 A | * | 7/1989 | Brockway et al. .......... 128/903 |
| 4,988,333 A | | 1/1991 | Engebretson et al. |
| 5,015,224 A | | 5/1991 | Maniglia |
| 5,015,225 A | | 5/1991 | Hough et al. |
| 5,070,535 A | | 12/1991 | Hochmair et al. |
| 5,095,904 A | | 3/1992 | Seligman et al. |
| 5,271,397 A | | 12/1993 | Seligman et al. |
| 5,277,694 A | | 1/1994 | Leysieffer et al. |
| 5,279,292 A | | 1/1994 | Baumann et al. |
| 5,403,262 A | | 4/1995 | Gooch |

(List continued on next page.)

FOREIGN PATENT DOCUMENTS

| | | |
|---|---|---|
| DE | 263 254 | 8/1912 |
| DE | 41 04 359 | 8/1992 |
| DE | 296 16 956 | 12/1996 |
| DE | 197 45 331 A1 | 4/1999 |
| DE | 199 14 993 | 7/2000 |
| EP | 0 190 836 | 8/1986 |
| EP | 0 200 321 | 11/1986 |
| EP | 0 400 900 | 12/1990 |
| EP | 0 537 385 | 4/1993 |

(List continued on next page.)

OTHER PUBLICATIONS

*Leadership in Engineering Manufacturing, Reliability, Quality and Performance*, Implantable Pulse Generators by Medtronic, Inc., Product Catalog Effective Feb. 1, 1977.
Catalog entitled *Medtronom*, Medrtronic, Copyright 1979.
Catalog entitled *Medtronom*, Medrtronic, Copyright 1980.

(List continued on next page.)

*Primary Examiner*—Max F. Hindenburg
*Assistant Examiner*—Jonathan Foreman
(74) *Attorney, Agent, or Firm*—Nixon Peabody LLP; David S. Safran

(57) ABSTRACT

The invention relates to an implantable medical device having an hermetically tight housing, which houses an electronic unit as well as an electrochemical energy storage for supplying the medical device with current. The energy storage is arranged directly within the hermetically tight housing without having a separate housing.

22 Claims, 2 Drawing Sheets

U.S. PATENT DOCUMENTS

| | | | |
|---|---|---|---|
| 5,411,467 A | | 5/1995 | Hortmann et al. |
| 5,545,219 A | | 8/1996 | Kuzma |
| 5,578,084 A | | 11/1996 | Kuzma et al. |
| 5,597,380 A | | 1/1997 | McDemott et al. |
| 5,601,617 A | | 2/1997 | Loeb et al. |
| 5,603,726 A | | 2/1997 | Schulman et al. |
| 5,624,376 A | | 4/1997 | Ball et al. |
| 5,626,629 A | | 5/1997 | Faltys et al. |
| 5,637,418 A | * | 6/1997 | Brown et al. ............... 429/127 |
| 5,697,975 A | | 12/1997 | Howard, III et al. |
| 5,788,656 A | | 8/1998 | Mino |
| 5,795,287 A | | 8/1998 | Ball et al. |
| 5,800,475 A | | 9/1998 | Jules |
| 5,814,095 A | | 9/1998 | Müller et al. |
| 5,957,958 A | | 9/1999 | Schulman et al. |
| 6,038,484 A | | 3/2000 | Kuzma |
| 6,067,474 A | * | 5/2000 | Schulman et al. ............ 607/33 |
| 6,143,440 A | | 11/2000 | Volz et al. |
| 6,146,778 A | * | 11/2000 | Rouillard et al. ............... 429/7 |
| 6,154,677 A | | 11/2000 | Leysieffer |
| 6,192,272 B1 | | 2/2001 | Fiedler |
| 6,227,204 B1 | | 5/2001 | Baumann et al. |
| 6,238,813 B1 | * | 5/2001 | Maile et al. ................. 429/176 |
| 6,251,062 B1 | | 6/2001 | Leysieffer |
| 6,269,266 B1 | | 7/2001 | Leysieffer |
| 6,358,281 B1 | * | 3/2002 | Berrang et al. ............... 600/25 |
| 6,381,336 B1 | * | 4/2002 | Lesinski et al. ............ 181/129 |
| 6,445,948 B1 | * | 9/2002 | Somdahl et al. ............... 607/2 |
| 6,450,172 B1 | * | 9/2002 | Hartlaub et al. ............ 128/899 |

FOREIGN PATENT DOCUMENTS

| | | |
|---|---|---|
| EP | 0 831 674 | 3/1998 |
| WO | WO 90/07251 | 6/1990 |
| WO | PCT/US90/00431 | 8/1990 |
| WO | WO 91/17638 | 11/1991 |
| WO | WO 96/00051 | 1/1996 |
| WO | WO 96/34508 | 10/1996 |

OTHER PUBLICATIONS

U.S. patent application Ser. No. 09/369,184, Leysieffer, filed Aug. 6, 1999.

Knör, "Tinnitus Retaining Therapy and Hearing Acoustics", pp. 26–27, Feb. 1997, Journal "Hoerakustik".

Suzuki et al., "Implantation of Partially Implantable Middle Ear Implant and the Indication", pp. 160–166, 1988, Adv Audiol., vol. 4.

Leysieffer et al., "A Totally Implantable Hearing Device for the Treatment of Sensorineural Hearing Loss: TICA LZ 3001", pp. 853–863, 1998, HNO vol. 46.

Lehner et al., "A Micromanipulator for Intraoperative Vibrator Hearing Tests with an Implantable Hearing Aid Transducers", pp. 507–512, 1998, HNO vol. 46.

Lehner et al., "An Osseointegrated Manipulator Device for the Positioning and Fixation of Implantable Hearing Aid Transducers", pp. 311–323, 1998, HNO vol. 46.

Baumann et al., "Basics of Energy Supply to Completely Implantable Hearing Aids for Sensorineural Hearing Loss", pp. 121–128, 1998, HNO vol. 46.

Lehner et al., "Elements for Coupling an Implantable Hearing Aid Transducer to the Ossicles or Perilymph by Col Deforation", pp. 27–37, 1998, HNO vol. 46.

Zenner et al., "First Implantations of a Totally Implantable Electronic Hearing System for Sensorineural Hearing Loss", pp. 844–852, 1998, HNO vol. 46.

Yanigahara et al., "Implantable Hearing Aid", pp. 869–872, Aug. 1987, Arch Otolaryngol Head Neck, Surg–Vol 113.

German Office Action, Dated: Jul. 4, 2001.

* cited by examiner

IMPLANTABLE MEDICAL DEVICE COMPRISING AN HERMETICALLY SEALED HOUSING

BACKGROUND OF THE INVENTION

1. Field of the Invention

The present invention in general relates to an implantable medical device comprising an hermetically sealed housing which houses an electronic unit and an electrochemical energy storage for supplying electrical current to the medical device. In particular the present invention to a hearing aid.

2. Description of Related Art

The active implants with which the present invention is concerned can be in particular systems for rehabilitation of a hearing disorder as they are further described in the prior art documents referred to in the following.

In recent years rehabilitation of sensorineural hearing disorders with partially implantable electronic systems has acquired major importance. In particular this applies to the group of patients in which hearing has completely failed due to accident, illness or other effects or is congenitally nonfunctional. If in these cases only the inner ear (cochlea) and not the neural auditory path which leads to the brain is affected, the remaining auditory nerve can be stimulated with electrical stimulation signals and thus a hearing impression can be produced which can lead to speech comprehension. In these so-called cochlear implants (CI) an array of stimulation electrodes which is controlled by an electronic system is inserted into the cochlea. This electronic module is encapsulated hermetically tightly and biocompatibly and is surgically embedded in the bony area behind the ear (mastoid). The electronic system, however, contains essentially only decoder and driver circuits for the stimulation electrodes. Acoustic sound reception, conversion of this acoustic signal into electrical signals and their further processing always take place externally in a so-called speech processor which is worn outside on the body. The speech processor converts the preprocessed signals coded accordingly onto a high frequency carrier signal which via inductive coupling is transmitted through the closed skin (transcutaneously) to the implant. The sound-receiving microphone always is located outside of the body and in most applications in a housing of a behind-the-ear hearing aid worn on the external ear and is connected to the speech processor by a cable. Such cochlear implant systems, their components and the principles of transcutaneous signal transmission are described, by way of example, in published European Patent Application No. 0 200 321 A2 and in U.S. Pat. Nos. 5,070,535, 4,441,210, 5,626,629, 5,545,219, 5,578,084, 5,800,475, 5,957,958 and 6,038,484. Processes of speech processing and coding in cochlear implants are described, for example, in published European Patent Application No. 0 823 188 A1, in European Patent 0 190 836 B1 and in U.S. Pat. Nos. 5,597,380, 5,271,397, 5,095,904, 5,601,617 and 5,603,726.

In addition to rehabilitation of congenitally deaf persons and those who have lost their hearing using cochlear implants, for some time, there have been approaches to offer better rehabilitation than with conventional hearing aids to patients with a sensorineural hearing disorder which cannot be surgically corrected by using partially or totally implantable hearing aids. In most embodiments the principle consists in stimulating via a mechanical or hydromechanical stimulus an ossicle of the middle ear or directly the inner ear, and not via the amplified acoustic signal of a conventional hearing aid in which the amplified acoustic signal is supplied to the external auditory canal. The actuator stimulus of these electromechanical systems is accomplished with different physical transducer principles, such as, for example, by electromagnetic and piezoelectric systems. The advantage of these processes is seen mainly in the sound quality which is improved as compared to conventional hearing aids, and for totally implanted systems, in the fact that the hearing prosthesis is not visible.

Such partially and filly implantable electromechanical hearing aids are described, for example, by Yanigahara and Suzuki et al. (Arch Otolaryngol Head Neck, Surg, Vol. 113, 1987, pp. 869–872; Hoke, M. (ed), Advances in Audiology, Vol. 4, Karger Basel, 1988), Lehner et al.: "Elements for coupling an implantable hearing aid transducer to the ossicles or perilymph by cold deformation", in HNO Vol. 46, 1998, pages 27–37; Baumann et al.: "Basics of energy supply to completely implantable hearing aids for sensorineural hearing loss", in HNO Vol. 46, 1998, pp. 121–128; Lehner et al.: "An osseointegrated manipulator device for the positioning and fixation of implantable hearing aid transducers", in HNO Vol. 46, 1998, pp. 311–323; Lehner et al.: "A micromanipulator for intraoperative vibratory hearing tests with an implantable hearing aid transducers", in HNO Vol. 46, 1998, pp. 507–512; Zenner et al.: "First implantations of a totally implantable electronic hearing system for sensorineural hearing loss", in HNO Vol. 46, 1998, pp. 844–852; Leysieffer et al.: "A totally implantable hearing device for the treatment of sensorineural hearing loss: TICA LZ 3001", in HNO Vol. 46, 1998, pp. 853–863; and are described in numerous patent documents, among others in published European Patent Application No. 0 263 254, in commonly owned U.S. Pat. Nos. 5,277,694 and 5,411,467 which are hereby incorporated by reference, as well as in U.S. Pat. Nos. 3,764,748, 4,352,960, 5,015,225, 5,015,224, 3,557,775, 3,712,962, 4,988,333 and 5,814,095.

Many patients with inner ear damage also suffer from temporary or permanent noise impressions (tinnitus) which cannot be surgically corrected and against which up to date there are no approved drug treatments. Therefore so-called tinnitus maskers are known. These devices are small, battery-driven devices which are worn like a hearing aid behind or in the ear and which, by means of artificial sounds which are emitted via for example a hearing aid speaker into the auditory canal, psychoacoustically mask the tinnitus and thus reduce the disturbing noise impression if possible to below the threshold of perception. The artificial sounds are often narrow-band noise (for example, tierce noise) which can be adjusted in its spectral position and its loudness level via a programming device to enable adaptation to the individual tinnitus situation as optimum as possible. In addition, there since recently exists the so-called retraining method in which by combination of a mental training program and presentation of broadband sound (noise) near the auditory threshold in quiet the perceptibility of the tinnitus is likewise supposed to be largely suppressed (H. Knoer "Tinnitus retraining therapy and hearing acoustics" journal "Hoerakustik" 2/97, pages 26 and 27). These devices are also called "noisers".

In the two aforementioned methods for hardware treatment of tinnitus, hearing aid-like, technical devices must be carried visibly outside on the body in the area of the ear; which devices stigmatize the wearer and therefore are not willingly worn.

U.S. Pat. No. 5,795,287 describes an implantable tinnitus masker with direct drive of the middle ear for example via an electromechanical transducer coupled to the ossicular chain. This directly coupled transducer can preferably be a so-called "Floating Mass Transducer" (FMT). This FMT corresponds to the transducer for implantable hearing aids which is described in U.S. Pat. No. 5,624,376.

In commonly owned co-pending U.S. Patent applications Ser. Nos. 09/372,172 and 09/468,860 which are hereby incorporated by reference implantable systems for treatment of tinnitus by masking and/or noiser functions are described, in which the signal-processing electronic path of a partially or totally implantable hearing system is supplemented by corresponding electronic modules such that the signals necessary for tinnitus masking or noiser functions can be fed into the signal processing path of the hearing aid function and the pertinent signal parameters can be individually adapted to the pathological requirements by further electronic measures. This adaptability can be accomplished by the necessary setting data of the signal generation and feed electronics being stored or programmed by hardware and software in the same physical and logic data storage area of the implant system, and the feed of the masker or noiser signal into the audio path of the hearing implant can be controlled via the corresponding electronic actuators.

Further systems for masking tinnitus are known for example from German utility model No. 296 16 956, published European Patent Applications Nos. 0 537 385 A1 and 0 400 900 A1, WO 91/17638, W096/00051, WO 90/07251, DE 41 04 359 C2 and from U.S. Pat. Nos. 5,697,975, 5,788,656 and 5,403,262.

For all of the above rehabilitation devices it today appears to be very sensible to design the systems such that they can be implanted completely. Depending on the desired function, such hearing systems are comprised of three or four functional units: a sensor (microphone) which converts the incident airborne sound into an electrical signal, an electronic signal processing, amplification and implant control unit, an electromechanical or implantable electroacoustic transducer which converts the amplified and preprocessed sensor signals into mechanical or acoustic vibrations and sends them via suitable coupling mechanisms to the damaged middle and/or inner ear, or in the case of cochlear implants a cochlear stimulation electrode, and an electric power supply system which supplies the aforementioned modules. Furthermore, there can be an external unit which makes available electrical recharging energy to the implant when the implant-side power supply unit contains a rechargeable (secondary) battery. Especially advantageous devices and processes for charging of rechargeable implant batteries are described in commonly owned co-pending U.S. patent application Ser. No. 09/311,566 and in commonly owned U.S. Pat. No. 5,279,292 which are hereby incorporated by reference. Preferably there can also be a telemetry unit with which patient-specific, audiological data can be wirelessly transmitted bidirectionally or programmed in the implant and thus permanently stored, as was described by Leysieffer et al.: "A totally implantable hearing device for the treatment of sensorineural hearing loss: TICA LZ 3001", in HNO Vol. 46, 1998, pp. 853–863.

In addition to the above fields of application of the present invention, the active implants may also be comprised of other systems for rehabilitation of a bodily disfunction, such as cardiac pacemakers, defibrillators, drug dispensers, nerve or bone growth stimulators, neurostimulators, pain suppression devices, and the like, wherein a secondary, rechargeable, electrochemical cell is used as energy source for operation.

In above incorporated U.S. Pat. No. 5,279,292 there is disclosed an implantable hearing system in which, in accordance with a first embodiment, control electronics for the actuator of the hearing system as well an energy storage which can be recharged from an external transmitter coil via a receiving coil are disposed within an implantable housing. In accordance with a second embodiment the control electronics is housed within a separate implantable housing which is connected via a plug connection with the implantable housing that contains the receiving coil and the rechargeable energy storage.

From commonly owned U.S. Pat. No. 6,192,272 which is hereby incorporated by reference there is known an implantable hearing system in which an electrochemical energy storage is disposed within a housing that preferably is hermetically sealed and which in turn is housed together with a control unit and a telemetry unit within an implantable housing. The energy storage can be a primary cell or a secondary cell, and in both cases can be a lithium based cell having a solid polymer electrolyte.

From commonly owned U.S. Pat. No. 6,143,440 which is hereby incorporated by reference there is known an implantable hearing system in which a rechargeable electrochemical energy storage is disposed within an hermetically tight housing. An electronic unit for monitoring the charging of the energy storage as well as a receiving coil for charging the energy storage are housed in separate housing. The hermetically tight housing of the energy storage is provided with a mechanical detector unit which is mechanically responsive to deformation due to the escaping of gas from the energy storage and which interrupts the charging process to prevent damage of the energy storage and of the housing due to impermissible operating states of the energy storage.

In commonly owned co-pending U.S. patent application Ser. No. 09/359,050 which is hereby incorporated by reference there is described an implantable hearing system, wherein a rechargeable, electrochemical energy storage which is provided with a housing is arranged within an hermetically tight housing which is equipped with a mechanical monitoring arrangement responsive to impermissible escape of gas from the energy storage and which then, if necessary, interrupts the charging process to prevent damage to the energy storage or the housing. The hermetically tight housing is arranged within a further hermetically tight housing which in accordance with a first embodiment additionally comprises an electronic unit for controlling the charging and discharging process, means for supplying a charging current and an additional electronic unit for monitoring mechanical housing monitoring arrangement. In accordance with a second embodiment these components are arranged within a separate housing, which further contains the control electronics of the hearing systems. The hermetically tight housing which contains the hermetically tight housing of the energy storage is connected to the main housing which contains the control electronics by means of a releasable, rigid mechanical connection.

From commonly owned U.S. Pat. No. 6,154,677 which is hereby incorporated by reference there is known an implantable hearing system wherein in accordance with a first embodiment a rechargeable electrochemical energy storage having a housing is arranged within an hermetically tight housing, which is provided with mechanical monitoring means responsive to impermissible escape of gas from the energy storage. In accordance with a first embodiment this hermetically tight housing of the energy storage is connected via a cable connection with an implantable main housing which contains an energy receiving coil, a corresponding electronics for control of the charging and discharging process as well as the control electronics for the hearing system. In accordance with a second embodiment the hermetically tight housing of the energy storage is housed, together with the components mentioned above, within the main housing.

From commonly owned U.S. Pat. No. 6,227,204 which is hereby incorporated by reference there is known an implantable hearing system in which the electronic unit for monitoring and controlling the charging process is designed such that the charging of the electrochemical energy storage is done dependent on the internal resistance of the energy storage, wherein during a first charging phase a constant charging current flows and during a second charging phase the charging current is adjusted such that the cell voltage that is measured during the charging process is maintained approximately at a predetermined constant value.

In commonly owned co-pending U.S. patent application Ser. No. 09/627,449 which is hereby incorporated by reference there is described an implantable hearing system with a rechargeable, electrochemical energy storage wherein the electrodes of the energy storage are arranged directly, i.e. without additional housing in an hermetically tight housing that is monitored by means of a mechanical unit responsive to impermissible gas evolution within the housing and which then mechanically interrupts the charging process. Furthermore, a temperature sensor is provided within the housing to monitor the operational state of the energy storage and, if applicable, to electronically interrupt the charging process by means of a monitoring electronics. The monitoring electronics can also be caused by the mechanical monitoring unit to interrupt the charging process. Apart form the energy storage and the temperature sensor, the monitored, hermetically tight housing of the energy storage does not contain any further components.

In commonly owned co-pending U.S. patent application Ser. No. 09/809,087 which is hereby incorporated by reference there is described a device and a process for operating a rechargeable storage for electrical energy, wherein the charging strategy of the energy storage is determined dependent on an adaptive model which takes into account data describing the state of the energy storage before start-up as well as data acquired during operation, and wherein the charging strategy can be automatically and continuously optimized using the data acquired during operation.

In commonly owned co-pending U.S. patent application Ser. No. 09/824,242 which is hereby incorporated by reference there is described an implantable energy storage arrangement for a medical implant comprising a monitoring unit that is independent of a unit for controlling the charging process and that detects the voltage of the energy storage independent of the control unit and is designed such that it assumes control over the charging path when a sensed storage voltage lies outside of a predetermined range.

In commonly owned co-pending U.S. patent application Ser. No. 09/824,212 which is hereby incorporated by reference there is described an implantable energy storage arrangement for a medical implant comprising means that is externally activatable to bypass an actuator within the charging path.

In commonly owned co-pending U.S. patent application Ser. No. 09/369,184 which is hereby incorporated by reference there is described a fully implantable hearing system for rehabilitation of a pure sensorineural hearing loss or combined conduction and inner ear hearing impairment, which system comprises at least one implantable sensor which generates an electrical audio signal, at least one signal processing and amplification unit in an audio-signal processing electronic hearing system path, at least one implantable electromechanical transducer and a unit for supplying power for the implant system, which power supply unit may comprise a secondary, rechargeable element. The hearing system is furthermore provided with an implant-side measurement unit which acquires the electrical sensor signal(s) electronically by measurement engineering and electronically conditions the signal(s). Also, a wireless telemetry unit is provided on the implant side which transfers the electronically conditioned sensor signal(s) to the outside to an external display and/or evaluation unit. In a preferred embodiment the signal processing and amplification unit, the implant-side measurement unit for generating and feeding the signals necessary for the audiometry function and the telemetry unit are housed together with the power supply unit in a hermetically tight and biocompatible implant housing to form an electronic module.

When the electrochemical secondary cell(s) is/are arranged within a separate hermetically gas tight protective housing that prevents the escape of substances from the cell which might be toxic to the electronics of the implant system and/or of gases which might damage the electronics and/or might lead to an impermissible pressure rise within the implant housing, and/or if a detector is provided that is in mechanical connection with the protective housing of the cell and which interrupts further supply of energy during the charging process and/or also interrupts the discharging process in cases of an impermissible or unwanted operational state, such additional protective measures cause additional costs, are troublesome in particular from a constructional point of view and increase the space requirements of an active implant. The latter can be of particular disadvantage when the implant is to be applied to a body region in which, by nature, there is only very little space available. This applies in particular to the implants for rehabilitation of a hearing disorder which were described in detail above, wherein in most cases the electronic module is positioned in the region of the mastoid on the scull cap, in which case the requirement is of particular concern that the size of the implant should be as small as possible. Especially in such a case the protective measures mentioned above are of particular disadvantage because often space in the direction of the height of the implant is required.

SUMMARY OF THE INVENTION

The primary object of the present invention is to devise an implantable medical device that is constructed as simple as possible but yet provides for sufficient operational safety with respect to the energy storage.

In accordance with the invention this object is achieved in that in an implantable medical device comprising an hermetically sealed housing which houses an electronic unit and an electrochemical energy storage for supplying electrical current to the medical device, the energy storage is disposed directly within the hermetically sealed housing and does not have a separate housing. The solution in accordance with the invention is advantageous in that due to the energy storage being arranged directly within the hermetically sealed housing and not having a separate housing, the construction is made more simple and therefore the production of the implantable medical device is facilitated.

In preferred embodiments of the invention the energy storage is a lithium based battery with solid electrolyte system, which battery is monitored with respect to its operational state by the electronic unit to prevent damage of the electronic unit. This is of particular importance when the energy storage is a rechargeable battery. Preferably the electronic unit further serves to control the medical device.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
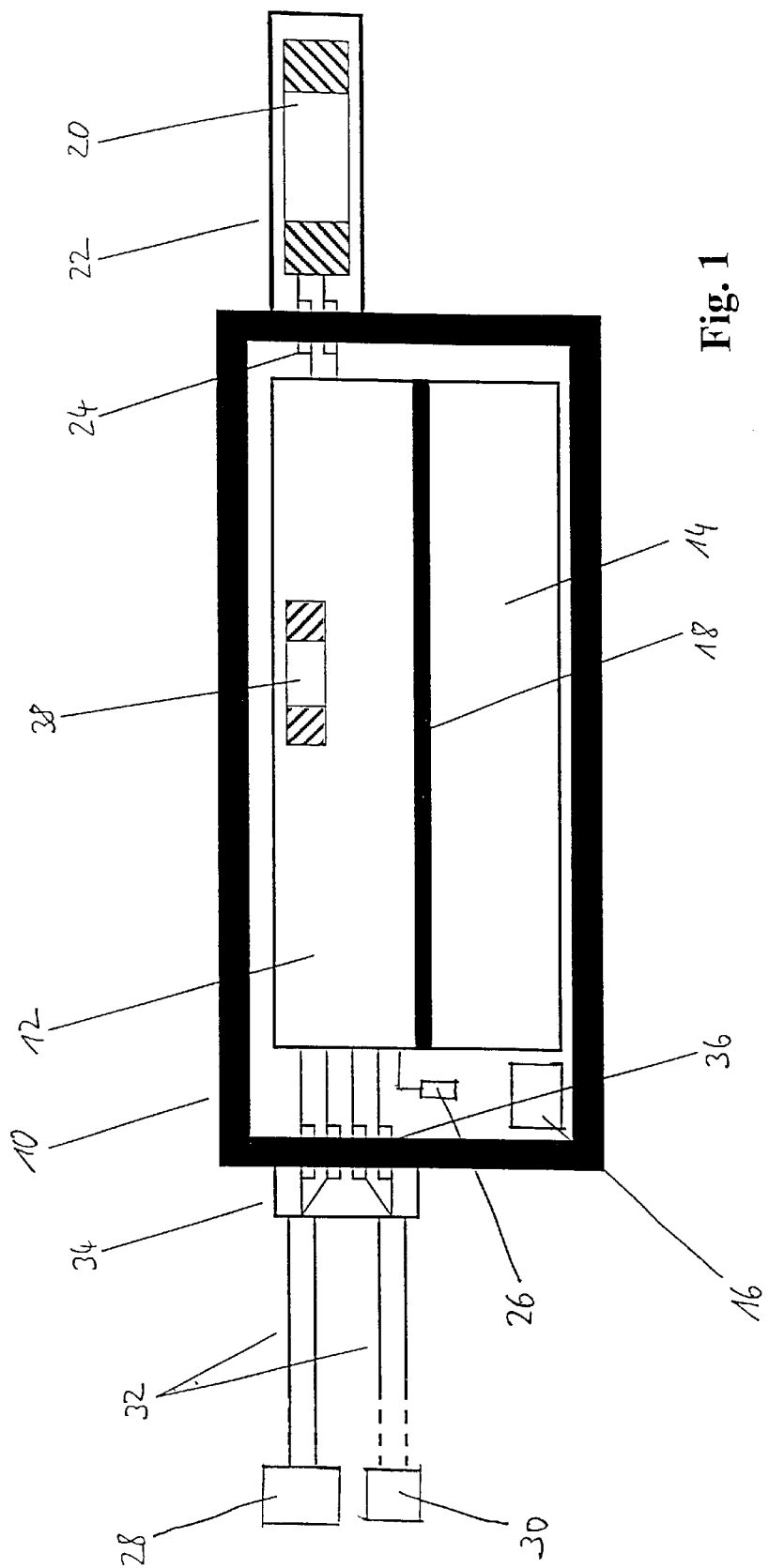
FIG. 1 schematically shows, in part in sectional view, a first embodiment for the structure of an implantable medical device in accordance with the invention.

In the embodiment shown in FIG. 1 an implantable, biocompatible, hermetically tight housing 10 houses an electronic unit 12 and a rechargeable electrochemical secondary cell 14. The secondary cell preferably is a lithium based battery with solid electrolyte system, such as a polymer electrolyte system. The anode of the battery 14 can be a lithium metal or lithium alloy electrode, whereas the cathode can be for example an inorganic or organic interstitial or redox electrode. Alternatively the anode also may be comprised of a lithium intercalation electrode. These systems are characterized in that at least when an electronic monitoring of the battery state is provided for, i.e. monitoring the state of the battery by monitoring certain electric parameters, disadvantageous evolution of gas may be prevented, which could be a hazard for the electronic unit 12 or could lead to an impermissible high pressure within housing 10.

In addition to electronically monitoring the battery 14 as will be described below, means 16 for binding gas can be provided within housing 10, to bind, i.e. adsorb, gas which might escape from battery 14. Preferably the gas binding means 16 can comprise a molecular sieve adsorbent (such materials are known as zeolites). In this manner gas possibly escaping from battery 14 can be bound at least to a certain extent and hence the internal pressure of housing 10 can be kept low.

Electronic unit 12 and battery 14 are mounted on opposing sides of a mechanical support or carrier 18, which in the present embodiment is in the shape of a plate. Carrier 18 can for example be designed as a printed circuit board, on which the electric components of the electronic unit 12 are mounted in surface mount technique (SMD). The electronic unit 12 or at least parts thereof can be mounted on carrier 18 in integrated form. When the battery 14 comprises a solid polymer electrolyte, the battery 14 may be assembled in layers on the opposite side of carrier plate 18. The electronic unit 12 is connected to the battery 14 through carrier 18.

A receiving coil 20 is arranged at a narrow face of the hermetically tight housing 10 within a biocompatible polymer enclosure 22, with the receiving coil 20 being connected with the electronic unit 12 via hermetic signal feed-throughs 24. Coil 20 is arranged so as to project from the narrow face of housing 10 and to be in mechanical connection with housing 10, for example by means of gluing, forming or molding. The design of receiving coil 20 shown is known for example from above-incorporated U.S. Pat. No 6,154,677.

Since housing 10 does not contain coil 20 as shown, it can be formed of metal, with the outer side thereof being provided with a biocompatible coating. Charging coil 20 serves to recharge battery 14 if the charging state thereof falls under a lower limit, wherein receiving coil 20 is transcutaneously supplied with electrical energy via a transmitter coil of an external charging device (not shown). Such an arrangement is shown for example in above-incorporated U.S. Pat. No. 5,279,292.

The electronic unit 12 is designed such as to comprise a unit which monitors charging and discharging of battery 14. This is done in that, during the charging process, the electronic unit 12 measures the charging current by means of a shunt resistance as well as the voltage of battery 14. A charging process based on this principle is described in above-incorporated U.S. Pat. No. 6,227,204, wherein at the start-up of the charging process the charging current is controlled such that a relatively high charging current may flow which is restricted to a predetermined higher limit. As soon as the measured battery voltage reaches a predetermined limit (wherein not the no-load voltage is measured but rather the voltage at a flowing charging current), in a second charging phase the charging current is adjusted such that the measured battery voltage is maintained at at least approximately a predetermined constant value which at least roughly corresponds to the value of the voltage reached at the end of the first charging phase. The charging process is terminated as soon as the measured change over time of the charging current falls below a predetermined minimum value. The control of the charging current can be effected for example by means of pulse width modulation or a resistance with controlled voltage. Thereby charging of the battery is regulated in dependency of the internal resistance of the battery. Thus it is guaranteed that only as much energy is supplied to the battery as is allowable for the electrochemical state, without extensive gas evolution or warming-up of the cell. In this manner hazardous operation states are prevented which could lead to damage of electronics 12 due to the escape of gas or to an extensive pressure rise within housing 10. The charging strategy automatically is adapted to aging phenomenons of the cell by adapting the charging strategy to the internal resistance of battery 14. In addition, a temperature sensor may be provided, as is indicated in FIG. 1 at 26, the signal of which also is considered in monitoring the charging process to thus detect and prevent an extensive warming-up of battery 14.

As soon as during operation the voltage that is measured over battery 14 falls below a predetermined minimum value, the electronic unit 12 generates a signal to cause the implant wearer to conduct a charging process to prevent excessive discharging of battery 14. Concepts which serve to guarantee rechargeability of battery 14 also in the under voltage range are described in above-incorporated co-pending U.S. patent applications Ser. Nos. 09/824,242 and 09/824,212. A charging concept which can react in an even more flexible manner to variations of battery characteristics in time is described in above-incorporated co-pending U.S. patent application Ser. No. 09/809,087. Here basically the entire operational history of a specific battery is recorded based on voltage and current measurements and is evaluated by means of an adaptive model, so that the charging strategy can repeatedly be actualized and hence optimized.

The components described so far form part of an implantable hearing system which comprises a sensor unit 28, in particular in the form of a microphone, as well as an actuator unit 30, which for example can be an electromechanical transducer which can be coupled mechanically to the ossicular chain or hydromechanically to the liquid filled spaces of the inner ear. Such transducers are described in detail for example in U.S. Pat. Nos. 5,277,694 and 5,411,467 and in commonly owned published European patent application No. 0 831 674 and do not require any further description herein. Electronic unit 12 is designed such that it constitutes the control unit for actuator 30 and which basically comprises a processing stage for the signals supplied by transducer 28 as well as an amplification stage to operate actuator 30. The control unit further comprises a microcontroller as well as analog-to-digital-converters. The microcontroller also may be used for monitoring and controlling the charging process.

At least actuator 30 is designed as implant and is connected via implant lines 32, a plug connection 34 as well as hermetical signal feed-throughs 36 to the electronic unit 12. Similarly, sensor 28, which likewise may be implantable is connected via lines 32, the plug connection 34 as well as hermetical signal feed-throughs 36 with electronic unit 12.

The battery 14 does not have a housing for its own. Rather it is arranged directly within hermetically tight housing 10, which thus facilitates the production of the system. By selecting the appropriate battery type (see above) and by providing an electronic monitoring of the charging process as well as optional additional measures, such as the provision of gas binding means 16, escape of impermissible amounts of gas from the battery 14 can be reliably prevented. Therefore, redundant mechanical monitoring of the hermetically tight housing 10, for example by means of a mechanical sensor and a switch which respond to a pressure rise within the housing, is not required, which allows for a compact design of housing 10 and for facilitated production thereof For applications that consume only little energy, the battery 14 can be a (non-rechargeable) primary battery rather than a (rechargeable) secondary battery, in which case, of course, no monitoring function for a charging process is implemented. Instead the electronic unit 12 can be provided with a function which displays the charging state of the primary battery, for example in terms of the remaining duration of operation until exhaustion of the battery.

The electronic unit 12 further can be connected to a data telemetry coil 38 to enable an exchange of data with a data transmitting device external to the body. In this manner for example the program which controls actuator 30 can be actualized, if necessary, or can be adapted to the specific circumstances of the implant wearer. Such an actualization of data of programs also can relate to the monitoring program of the charging process.

Figure 2:
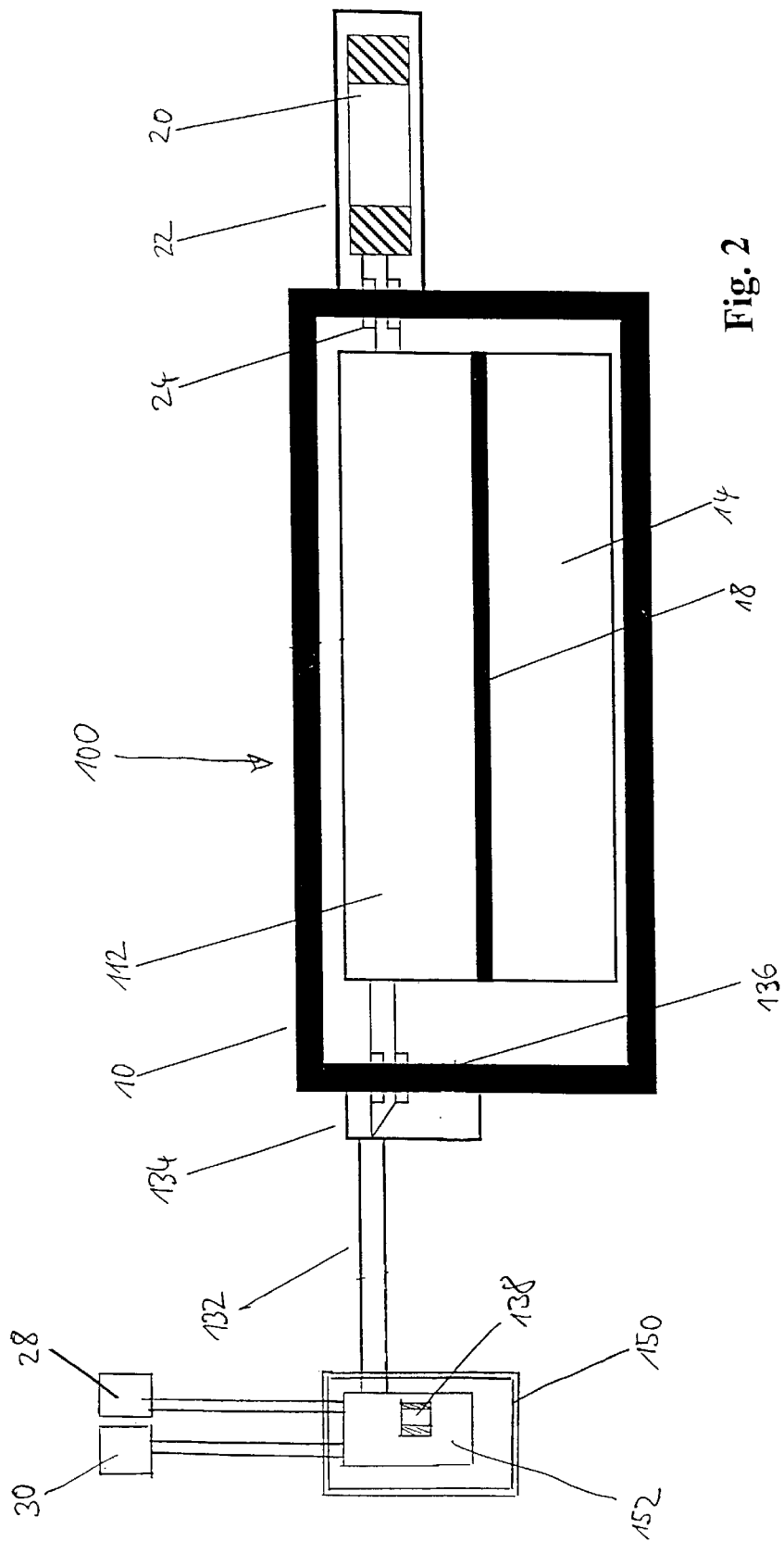
FIG. 2 shows in a view similar to that of FIG. 1 a second embodiment for the structure of an implantable medical device in accordance with the invention.

In FIG. 2 there is shown an alternative embodiment which differs from the embodiment shown in FIG. 1 basically in that the portion of the electronic unit which controls the operation of actuator 30 is arranged in a separate biocompatible, implantable, hermetically tight housing 150. This control electronics is designated with reference sign 152. Housing 150 furthermore contains a data telemetry coil 138. The control electronics 152 is connected with the charging electronics 112 via conduits 132, a plug connection 134 as well as hermetical feed-throughs 136, wherein charging electronics 112 performs the monitoring and control functions described above during the charging process of battery 14. Temperature sensor 26, gas binding means 16 as well as charging receiving coil 20 correspond to those of FIG. 1. In the embodiment of FIG. 2 housing 10 together with the components contained therein or attached thereto constitutes an energy supply module 100 for control unit 152. The energy supply module 100 can also be directly connected to housing 150 of the control unit 152, rather than via a plugable cable connection 132. In this case a coupling member is provided which provides for a releasable, rigid mechanical connection of energy supply module 100 to housing 150. Such coupling member simultaneously serves to provide for a releasable galvanic connection of battery 14.

If the battery 14 is a primary battery, the electronic unit 112 which was described in connection with the embodiment shown in FIG. 1 can be provided with a function for displaying the charging state rather than with a function for monitoring the charging process.

Control unit 12 or 112, respectively, can be designed such that it controls the energy delivery within battery 14 or that it apportions it to the individual consumers.

While several embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. An implantable medical device comprising a hermetically sealed housing which is constructed of a size and of materials suitable for implantation in a living being and which houses an electronic unit and an electrochemical energy storage for supplying electrical current to the medical device, wherein the energy storage is disposed directly within the hermetically sealed housing and does not have a separate housing.

2. The device as claimed in claim 1 wherein the energy storage is a battery with solid electrolyte system.

3. The device as claimed in claim 2 wherein the energy storage is a lithium based battery.

4. The device as claimed in claim 1 wherein the electronic unit is a unit for monitoring the energy storage.

5. The device as claimed in claim 4 wherein the electronic unit further controls the delivery of energy from the energy storage.

6. The device as claimed in claim 1 wherein the electronic unit is a unit for controlling the medical device.

7. The device as claimed in claim 6 wherein the electronic unit further is adapted for control of the energy storage.

8. The device as claimed in claim 1 wherein the energy storage is a primary battery.

9. The device as claimed in claim 1 wherein the energy storage is a secondary battery.

10. The device as claimed in claim 9 wherein the electronic unit is adapted to monitor and control charging of the energy storage such that an operational state of the energy storage is maintained within a predetermined range in which damage of the energy storage and escape of gas are substantially prevented.

11. The device as claimed in claim 10 wherein the electronic unit is adapted to interrupt the charging when the operational state of the energy storage is impending to leave the predetermined range.

12. The device as claimed in claim 2 wherein the energy storage and the electronic unit are mounted on a common support.

13. The device as claimed in claim 12 wherein the support is in the shape of a plate and wherein the energy storage and the electronic unit are mounted on different sides of the support.

14. The device as claimed in claim 1 wherein the hermetically sealed housing comprises means to bind gas which possibly might leave the energy storage.

15. The device as claimed in claim 14 wherein the gas binding means comprises an adsorption material.

16. The device as claimed in claim 15 wherein the adsorption material comprises molecular sieve material.

17. The device as claimed in claim 9 comprising a receiving coil to which energy may be electromagnetically fed transcutaneously from an external charging device to recharge the energy storage.

18. The device as claimed in claim 17 wherein the receiving coil is disposed in a biocompatible polymer enclosure at the outer side of the hermetically sealed housing and is in mechanical connection with the housing.

19. The device as claimed in claim 18 wherein the receiving coil is disposed at the narrower face of the hermetically sealed housing so as to project therefrom.

20. The device as claimed in claim 1 wherein the electronic unit comprises a coil for exchanging data with an external telemetry unit for controlling the medical device.

21. The device as claimed in claim 1 wherein the hermetically sealed housing is provided at the outer side thereof with feed-through contacts for a sensoric component and an actoric component.

22. The device as claimed in claim 1 wherein the medical device is a hearing aid.

* * * * *